United States Patent [19]

Takeda et al.

[11] Patent Number: 5,071,870

[45] Date of Patent: Dec. 10, 1991

[54] TRIOXANE COMPOSITION AND INSECT-PROOFING AGENT

[75] Inventors: Mutsuhiko Takeda, Tokyo; Minoru Kakuda, Matsudo; Kiyoshi Yoshida, Tokyo; Toshie Takahashi, Matsudo; Masafumi Shimpo, Kashiwa, all of Japan

[73] Assignee: Mitsubishi Gas Chemical Co., Inc., Tokyo, Japan

[21] Appl. No.: 343,420

[22] Filed: Apr. 26, 1989

[30] Foreign Application Priority Data

Apr. 26, 1988 [JP] Japan .................................. 63-101400
Jun. 8, 1988 [JP] Japan .................................. 63-139543

[51] Int. Cl.$^5$ ..................... A01N 43/32; A01N 47/10
[52] U.S. Cl. ...................................... 514/452; 514/479
[58] Field of Search ................................ 514/452, 479

[56] References Cited

U.S. PATENT DOCUMENTS 801,855  10/1905  Drefus ................................. 422/305
2,464,043  3/1949  Kamlet ............................... 424/76.2
3,097,129  7/1963  Laffetay et al. ..................... 514/690

FOREIGN PATENT DOCUMENTS 1577690  6/1969  France .
115802  1/1988  Japan .

OTHER PUBLICATIONS

King, Chemicals Evaluated as Insecticides and Repellants at Orlando, Fla. (May 1954), pp. 1-3, 13-16 & 106.

*Primary Examiner*—Allen J. Robinson
*Attorney, Agent, or Firm*—Sherman and Shalloway

[57] ABSTRACT

Disclosed is a composition comprising trioxane and an assistant aiding in the insect-proofing action of trioxane or controlling its vapor pressure.

1 Claim, No Drawings

TRIOXANE COMPOSITION AND INSECT-PROOFING AGENT

BACKGROUND OF THE INVENTION

1. Field of the Invention

This invention relates to a composition comprising trioxane and an assistant aiding in the insect-proofing action of trioxane or controlling its vapor pressure. The invention also relates to an insect-proofing agent composed of this composition.

2. Description of the Prior Art

Sublimable substances such as camphor, naphthalene and p-dichlorobenzene have been used as insect-proofing agents for clothes.

These conventional sublimable substances have the defect of giving off inherent irritating odors which remain in clothes after storage. Camphor and naphthalene have a weak action on clothes harmful insects such as case-making clothes moth (*Tinea pellionella* Linne) and various carpet beetles such as *Attagenus piceus* Oliv and *Arthrenus verbasci* Linne. p-Dichlorobenzene has toxicity and causes environmental pollution, and it has been desired to reduce its amount of use.

The present inventors previously filed a patent application for an insect-proofing agent comprising 1,3,5-trioxane (simply "trioxane" hereinafter) as an active ingredient (Japanese Laid-Open Patent Publication No. 115802/1988). Trioxane exhibits an insect-proofing action even when used alone. If, however, it is possible to increase its insect-proofing action further, its amount used would be able to be decreased.

SUMMARY OF THE INVENTION

The present inventors undertook extensive investigations in order to obtain an insect-proofing agent having a higher insect-proofing action, and found that by mixing trioxane with a certain assistant, a composition can be obtained which has higher insect-proofing action than trioxane used singly. This finding has now led to the accomplishment of the present invention.

It is an object of this invention therefore to provide a novel trioxane composition having an excellent insect-proofing action which continues for a long period of time, and to provide a sublimable insect-proofing agent composed of this composition.

Another object of this invention is to provide a trioxane composition comprising trioxane and as an assistant a component capable of increasing the insect-proofing action of trioxane and controlling the sublimability of trioxane and its sublimation speed.

Still another object of this invention is to provide a trioxane composition whose flash point can be maintained higher than trioxane alone, and as a result, which is easy to store or handle.

A further object of this invention is to provide a sublimable insect-proofing agent which is particularly useful as a clothes insect-proofing agent and a household harmful insect repellent having an excellent insect-proofing action without involving the problem of toxicity and environmental pollution.

Thus, according to this invention, there is provided a trioxane composition comprising as active ingredients (A) 1,3,5-trioxane, and
(B) as an assistant, at least one compound selected from the group consisting of (i) a dibasic acid ester represented by the following formula $$R^3OOC(R^1)_n COOR^2 \quad (1)$$

wherein $R_1$ represents an alkylene group, carbon atoms, an alkylene group each having 2 to 6 or a phenylene group, n is 0 or 1, and each of $R^2$ and $R^3$ represents an alkyl group having not more than 4 carbon atoms, a cycloalkyl group or a phenyl group, (ii) a phenol represented by the following formula wherein $R^4$ represents an alkyl group, an alkenyl group or an alkoxy group each having not more than 4 carbon atoms, and m is a number of 1 to 3, and when m is a number of 2 or 3, $R^4$ may be same or different, (iii) an alcohol represented by the following formula $$R^5-Z^1-OH \quad (3)$$

wherein $Z^1$ represents an alkylene group having 1 to 2 carbon atoms, and $R^5$ represents a phenyl group, an alkylphenyl group, 1 to 3 hydroxyalkyl group or an alkoxy group, (iv) a monocarboxylic acid ester represented by the following formula $$R^6(Z^2)_l COOR^7 \quad (4)$$

wherein $R^6$ represents an amino group, a hydrazino group, a phenyl group, a hydroxyphenyl group or an acyloxyphenyl group, $Z^2$ represents an alkylene group, an alkenylene group or a hydroxyalkylene group each having up to 2 carbon atoms, and l is 0 or 1 or by the following formula wherein $R^8$ represents an alkylene group or a phenylenemethylene group each having 5 to 7 carbon atoms, (v) a diphenyl compound or a quinone represented by the following formula wherein p, q and s are zero or 1 with the proviso that at least one of them is 1, (vi) a substituted benzene compound represented by the following formula

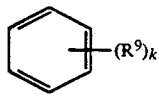

(7)

wherein $R^9$ is an alkyl group, an alkenyl group or an alkoxy group each having 1 carbon atom, and k is an integer of 2 to 4, (vii) an amide represented by the following formula

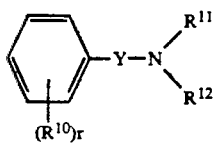

(8)

wherein Y represents =CO or =SO$_2$, each of $R^{11}$ and $R^{12}$ represents a hydrogen atom or an alkyl group having not more than 4 carbon atoms, $R^{10}$ represents an alkyl group having not more than 4 carbon atoms or an amino group, and r is a number of 0 or 1, (viii) a heterocyclic compound having a molecular weight of 90 to 200 and containing at least one atom selected from the group consisting of nitrogen, oxygen and sulfur atoms, and (ix) a terpene.

There is also provided a sublimable insect-proofing agent, particularly for clothes and household harmful insect repellent use, comprising the trioxane composition as an active ingredient.

DETAILED DESCRIPTION OF PREFERRED EMBODIMENTS

The assistants (i) to (ix) have common properties with respect to trioxane. Specifically, these assistants have the property of increasing the insect-proofing action of trioxane and in some cases, controlling the sublimability of trioxane. These assistants other than p-methylbenzylalcohol do not show an insect-proofing action or shown only a very low insect-proofing action when used singly, but when blended with trioxane, show a high insect-proofing action. The insect-proofing action is evaluated by a feed inhibition ratio on clothes, as will be shown in working examples given hereinafter. The combination of the components in this invention gives a higher feed inhibition ratio than in the case of using either component singly. The second property is closely related to the duration of the insect-proofing action, and furthermore, by using the assistant, the flash point of the composition can be rendered higher than trioxane alone.

The dibasic acid ester (i) is represented by formula (1). The alkylene group $R^1$ may be, for example, an ethylene or tetramethylene group. The alkenylene group $R^1$ may be, for example, a cis- or trans-vinylene group or propenylene group. Examples of the phenylene group are o-, m- or p-phenylene groups. The alkyl groups for $R^2$ and $R^3$ are preferably a methyl group, but may also be an ethyl, propyl or butyl group. The cycloalkyl group is preferably a cyclohexyl group. Suitable examples of the dibasic acid ester include dialkyl esters of aliphatic dicarboxylic acids having 2 to 8 carbon atoms benzenedicarboxylic acid esters, particularly dimethyl fumarate, diphenyl phthalate, dicyclohexyl phthalate, dimethyl isophthalate, dimethyl terephthalate, dimethyl oxalate and dimethyl itaconate.

The phenol (ii) is represented by general formula (2). Examples of the alkyl group $R^4$ include methyl, ethyl, isopropyl and butyl groups. The alkoxy group for $R^4$ may be, for example, a methoxy or ethoxy group. The alkenyl group for $R^4$ may be, for example, a vinyl or propenyl group. Suitable examples of the phenol (ii) include 2,4-dimethylphenol, 2,5-dimethylphenol, 2,6-dimethylphenol, 3,4-dimethylphenol, 3,5-dimethylphenol, 2,3,5-trimethylphenol, 2,4,6-trimethylphenol, 2,6-di-t-butyl-4-methylphenol, p-methoxyphenol, thymol and eugenol.

The alcohol (iii) is represented by general formula (3). It includes polyhydric alcohols, alkoxyalcohols and araliphtic alcohols. The hydroxyalkyl group for $R^5$ is preferably a sec- or tert-alkyl group having 1 to 3 hydroxyl groups. The alkoxy group preferably has 2 to 4 carbon atoms. Suitable examples of the alcohol (iii) are neopentyl glycol, 2-ethoxyethanol, pentaerythritol, p-methylbenzyl alcohol, and beta-phenethyl alcohol.

The monocarboxylic acid ester (iv) includes carbamic acid esters, carbazinic acid esters and araliphatic acid esters of general formula (4), and cyclic esters, i.e. lactones, of general formula (5). Suitable examples of the compound (iv) are methyl cinnamate, methyl carbamate, methyl carbazate, methyl mandelate, methyl p-hydroxybenzoate, methyl acetylsalicylate, epsilon-caprolactone and phthalide.

The diphenyl compound or quinone (v) is represented by general formula (6). Examples of the diphenyl compound are benzophenone, benzoin and benzhydrole. Examples of the quinone are quinones having 6 to 14 carbon atoms, particularly anthraquinone.

The substituted benzene compound (vi) is represented by general formula (7), and particularly has 6 to 10 carbon atoms. Examples of the substituted benzene compound are p-dimethoxybenzene and 1,2,4,5-tetramethylbenzene.

The amide (vii) is represented by general formula (8), and includes, for example, aromatic carboxylic acid amides and sulfonic acid amides. Suitable examples are N,N-diethyl-m-toluamide and sulfanilamide.

The heterocyclic compound (viii) is alicyclic or aromatic compounds containing at least one nitrogen, oxygen or sulfur atom in a five-membered ring or a six-membered ring. The heterocycle may contain 1 or 2 fused benzene rings. Suitable examples include N-methylpyrrolidone, hydantoin, dibenzofurane, benzotriazole, indole, imidazole, triethylenediamine and sulfolene.

Terpenes generally having a molecular weight of 136 to 222, preferably (l)-menthol, linalool, geraniol and limonene, may be used as the terpene (ix).

If methyl cinnamate, methyl carbamate, dimethyl fumarate, dicyclohexyl phthalate, dimethyl isophthalate, dimethyl oxalate, p-methylbenzyl alcohol, benzophenone, p-methoxyphenol, thymol or sulfolene is used as an assistant in this invention, the vapor pressure of trioxane is moderately controlled. As a result, the resulting composition attains a moderately high flash point as compared with trioxane alone. Accordingly, such assistant can be more safely used as trioxane vapor generating agents.

Furthermore, a composition of this invention comprising at least one of methyl cinnamate, 1-menthol, linalool geraniol, limonene, beta-phenethyl alcohol and eugenol as assistants can be used suitably as a clothes insect-proofing agent because it has a fragrance.

1,3,5-Trioxane is a sublimable solid substance of the chemical formula $(CH_2O)_3$ which has a melting point of 64° C. and is stable at room temperature in air. Desirably, 1,3,5-trioxane used in this invention is of high purity. Desirable, its formic acid content is not more than 20 ppm, especially not more than 10 ppm, and its formaldehyde content is not more than 50 ppm, especially not more than 20 ppm.

The proportions of trioxane and the assistant in the composition of this invention can be varied over wide ranges. Generally, for the objects of this invention, the composition of this invention contain 5 to 99.8% by weight, especially 10 to 50% by weight, of trioxane (A) and 0.2 to 95% by weight, especially 50 to 90% by weight, of the assistant (B).

The composition of this invention may be suitably obtained by mixing trioxane with the assistant, melting the mixture to form a uniformly dispersed liquid, and cooling the liquid. The cooled composition may be liquid or solid. For example, a mixture of 50 parts by weight of trioxane and 50 parts by weight of dimethyl oxalate melts at 30° C. to form a liquid composition. Generally, however, the composition frequently becomes a solid in the room temperature. There is no particular restriction on the means for mixing the ingredients. For example, the assistant may be dispersed in molten trioxane or trioxane may be dispersed in a molten mass of the assistant. Alternatively, a powdery mixture of both may be co-melted. It should be understood that the composition of this invention is not limited to one obtained by mixing components (A) and (B) in the molten state, and may be a mixture of (A) and (B) in powder form.

The composition of this invention, either singly, or in combination with a known carrier such as silica gel or talc can be formulated in an insect-proofing agent, particularly one for clothes, or a household harmful insect repellent, in various forms. For example, the solid composition may be used in the form of a dust or a molded agent such as tablets, granules and balls. From the viewpoint of the moldability of the composition or the strength of the agent, binders, vehicles, lubricants, fillers, etc. may be incorporated. It is also possible to incorporate, perfumes, stabilizes and dyes. The liquid composition or a solution or dispersion of the composition in a solvent may be used as a liquid preparation by filling up it in a container or an aerosol container. It may also be used in a form occluded in a substrate such as paper or cloth, or in a filler, or may be formed into a solid by using a gelling agent, a resin, etc. and used as a gel or a solid agent.

The trioxane composition of this invention exhibts an excellent insecticidal action or an excellent feed inhibitory action on insects feeding on clothes and also an excellent insect-proofing action on household harmful insects as compared with trioxane alone, and these actions are long-lasting. Accordingly, the trioxane composition of this invention is suitably used as a clothes insect-proofing agent and a household harmful insect repellent.

The trioxane composition of this invention is easy to store or handle because its flash point can be made higher than the flash point of trioxane alone, In addition, the use of the trioxane composition of this invention can avoid the use of p-dichlorobenzene which gives rise to the problem of toxicity and environmental pollution.

The following examples illustrate the present invention more specifically.

EXAMPLE 1

In each run, 99 parts by weight of trioxane was mixed with 1 part by weight of an assistant. The mixture was melted in a hot water bath to form a uniform liquid. The liquid was cooled to 20° C. to form a solid composition.

The solid composition was processed in a pulverizer to form a uniform powdery trioxane composition.

The trioxane composition prepared was used in the following insect-proofing assay. Six milligrams of the trioxane composition was put at the bottom of a 900 ml. glass bottle. A metallic cage having a diameter of 3 cm containing ten 40-day old larvae of case-making clothes moth (*Tinea pellionella* Linne) and about 100 mg of square pieces of woollen fabrics each side measuring 3 cm was fixed at a position 5 cm above the composition. The bottle was then sealed up, and left to stand in a constant-temperature chamber at 30° C. for 135 hours. Then, the cage was taken out, and the mortality of the case-making clothes moth larvae, and the amount of eating damage on the woollen fabrics (weight loss) were examined.

The results are evaluated by kill ratio and feed inhibition ratio as follows:

$$\text{Kill ratio } (X, \%) = \frac{\text{Number of dead insects}}{\text{Number of tested insects}} \times 100$$

$$\text{Feed inhibition ratio } (Y, \%) = \frac{\substack{\text{Amount of eating damage of} \\ \text{woollen fabrics in an area treated} \\ \text{with the insect-proofing agent}}}{\substack{\text{Amount of eating damage} \\ \text{of woollen fabrics in} \\ \text{a non-treated area}}} \times 100$$

COMPARATIVE EXAMPLE 1

The same insect-proofing test as in Example 1 was conducted except that 6 mg of trioxane powder alone without an assistant was used.

CONTROL EXAMPLE 1

The same insect-proofing test as in Example 1 was conducted without using any insect-proofing agent.

The results are shown in Tables 1-(1) to 1-(4).

When each of the foregoing assistants was used in an amount of 0.06 mg, no insect-proofing effect was observed.

TABLE 1

| Run No. | Assistant | Kill ratio (%) | Amount of eating damage (mg) | Feed inhibition ratio (%) |
|---|---|---|---|---|
| 1 | methyl cinnamate | 0 | 14.4 | 62 |
| 2 | methyl carbamate | 20 | 11.7 | 69 |
| 3 | methyl carbazate | 20 | 9.8 | 74 |
| 4 | methyl acetyl-salicylate | 0 | 9.8 | 74 |
| 5 | dimethyl fumarate | 0 | 13.2 | 65 |
| 6 | diphenyl phthalate | 0 | 15.1 | 60 |
| 7 | dicyclohexyl phthalate | 40 | 11.3 | 70 |
| 8 | dimethyl isophthalate | 20 | 14.4 | 62 |
| 9 | dimethyl | 0 | 15.5 | 59 |

TABLE 1-continued

| Run No. | Assistant | Kill ratio (%) | Amount of eating damage (mg) | Feed inhibition ratio (%) |
|---|---|---|---|---|
| | terephthalate | | | |
| 10 | ε-caprolactone | 0 | 10.2 | 73 |
| 11 | N-methylpyrolidone | 0 | 13.6 | 64 |
| 12 | N,N-diethyl-m-toluamide | 0 | 14.4 | 62 |
| 13 | hydantoin | 0 | 15.1 | 60 |
| 14 | anthraquinone | 10 | 14.7 | 61 |
| 15 | benzoin | 0 | 8.3 | 78 |
| 16 | benzhydral | 0 | 11.7 | 69 |
| 17 | neopentyl glycol | 10 | 14.4 | 62 |
| 18 | 2-ethoxyethanol | 0 | 9.8 | 74 |
| 19 | 1,2,4,5-tetramethylbenzene | 0 | 11.7 | 69 |
| 20 | 2,4-dimethylphenol | 0 | 11.3 | 70 |
| 21 | 2,6-dimethylphenol | 0 | 11.3 | 70 |
| 22 | 3,4-dimethylphenol | 0 | 11.3 | 70 |
| 23 | 2,4,6-trimethylphenol | 0 | 3.4 | 91 |
| 24 | 2,6-di-t-butyl-4-methylphenol | 0 | 4.9 | 87 |
| 25 | benzotriazole | 0 | 15.5 | 59 |
| 26 | indole | 10 | 11.7 | 69 |
| 27 | triethylenediamine | 20 | 11.3 | 70 |
| 28 | sulfanilamide | 0 | 13.6 | 64 |
| 29 | sulfolene | 0 | 9.8 | 74 |
| 30 | (λ)-menthol | 0 | 15.9 | 58 |
| 31 | linalool | 0 | 4.9 | 87 |
| 32 | geraniol | 0 | 14.4 | 62 |
| 33 | limonene | 0 | 17.0 | 55 |
| 34 | β-phenethylalcohol | 0 | 9.1 | 76 |
| 35 | eugenol | 0 | 12.5 | 67 |
| Comparative Example 1 | trioxane alone | 0 | 20.8 | 45 |
| Control Example 1 | no agent | 0 | 37.8 | 0 |

EXAMPLE 2

In each run, 5 mg of powdery trioxane was mixed with a predetermined amount of an assistant in a petri dish to form a trioxane composition. The petri dish containing the prepared trioxane composition was placed at the bottom of a 900 ml glass bottle, and a metallic cage having a diameter of 3 cm containing ten 40-day old larvae of case-making clothes moth (*Tinea pellionella* Linne) and about 100 mg of square pieces of woollen fabrics each side measuring 3 cm was fixed at a position 5 cm above the composition. The bottle was then sealed up, and left to stand in a constant-temperature chamber at 30° C. for 120 hours. Then, the cage was taken out, and the mortality of the case-making clothes moth larvae, and the amount of eating damage on the woollen fabrics (weight loss) were examined. The run was conducted twice, and the averaged results are shown in Table 2-(1) and 2-(2).

COMPARATIVE EXAMPLE 2

The same insect-proofing test was conducted as in Example 2 except that trioxane was not used, and the assistants were singly used in the same amounts as used in Runs Nos. 36 to 55. The results are shown in Tables 3-(1) and 3-(2).

TABLE 2

| Run No. | Assistant | Amount of Assistant (mg) | kill ratio (%) | Amount of eating damage (mg) | Feed inhibition ratio (%) |
|---|---|---|---|---|---|
| 36 | methyl cinnanate | 9 | 40 | 6.7 | 80 |
| 37 | methyl mandelate | 2 | 30 | 9.7 | 71 |
| 38 | methyl p-hydroxybenzoate | 4 | 15 | 9.4 | 72 |
| 39 | methyl acetylsalicylate | 5 | 15 | 12.1 | 64 |
| 40 | dimethyl fumarate | 30 | 80 | 0.0 | 100 |
| 41 | dicyclohexyl phthalate | 50 | 25 | 10.4 | 69 |
| 42 | dimethyl isophthalate | 11 | 40 | 6.7 | 80 |
| 43 | dimethyl oxalate | 5 | 100 | 0.0 | 100 |
| 44 | epsilon-caprolactone | 3 | 75 | 2.7 | 92 |
| 45 | phthalide | 12 | 40 | 16.8 | 50 |
| 46 | benzophenone | 25 | 5 | 10.8 | 68 |
| 47 | benzhydrole | 40 | 15 | 6.7 | 80 |
| 48 | neopentyl glycol | 60 | 90 | 5.0 | 85 |
| 49 | penta-erythritol | 4 | 15 | 15.1 | 55 |
| 50 | 2,3,5-trimethylphenol | 8 | 55 | 14.4 | 57 |
| 51 | 2,6-di-t-butyl-4-methylphenol | 20 | 15 | 16.8 | 50 |
| 52 | p-methoxyphenol | 16 | 85 | 10.8 | 68 |
| 53 | dibenzofurane | 40 | 35 | 4.4 | 87 |
| 54 | (λ)-menthol | 1 | 80 | 5.4 | 84 |
| 55 | p-methyl benzyl alcohol | 12 | 100 | 0.0 | 100 |

TABLE 3

| Run No. | Assistant | Amount of Assistant (mg) | kill ratio (%) | Amount of eating damage (mg) | Feed inhibition ratio (%) |
|---|---|---|---|---|---|
| 136 | methyl cinnanate | 9 | 0 | 9.1 | 73 |
| 137 | methyl mandelate | 2 | 0 | 30.2 | 10 |
| 138 | methyl p-hydroxybenzoate | 4 | 0 | 30.9 | 8 |
| 139 | methyl acetylsalicylate | 5 | 5 | 30.2 | 10 |
| 140 | dimethyl fumarate | 30 | 60 | 1.7 | 95 |
| 141 | dicyclohexyl phthalate | 50 | 0 | 30.2 | 10 |
| 142 | dimethyl isophthalate | 11 | 0 | 31.9 | 5 |
| 143 | dimethyl oxalate | 5 | 70 | 1.7 | 95 |
| 144 | epsilon-caprolactone | 3 | 30 | 30.9 | 8 |
| 145 | phthalide | 12 | 0 | 33.6 | 0 |
| 146 | benzophenone | 25 | 0 | 26.5 | 21 |
| 147 | benzohydrole | 40 | 0 | 31.9 | 5 |
| 148 | neopentyl glycol | 60 | 0 | 33.3 | 1 |
| 149 | pentaerythritol | 4 | 0 | 33.6 | 0 |
| 150 | 2,3,4-trimethylphenol | 8 | 10 | 26.9 | 20 |
| 151 | 2,6-di-t-butyl-4-methylphenol | 20 | 0 | 33.6 | 0 |
| 152 | p-methoxyphenol | 16 | 40 | 26.9 | 12 |
| 153 | dibenzofurane | 40 | 0 | 15.8 | 53 |
| 154 | (λ)-memthol | 1 | 50 | 20.2 | 40 |
| 155 | p-methyl-benzyl alcohol | 12 | 80 | 11.5 | 66 |

COMPARATIVE EXAMPLE 3

The same experiment as in Example 2 was conducted by using 5 mg of trioxane without adding an assistant. The results are shown in Table 4.

CONTROL EXAMPLE 2

The same experiment as in Example 2 was conducted except that no insect-proofing agent was used. The experiment was conducted twice, and the averaged results are shown in Table 4.

TABLE 4

| Ex. No. | Insect-proofing agent | Kill ratio (%) | Amount of eating damage (mg) | Feed inhibition ratio (%) |
| --- | --- | --- | --- | --- |
| Comparative Example 3 | trioxane alone | 0 | 21.8 | 35 |
| Control Example 2 | None | 0 | 33.6 | 0 |

EXAMPLE 3

In each run, predetermined amounts of trioxane and an assistant were mixed and melted in a hot water bath to form a uniform liquid. 0.1 g of the liquid was taken out, and impregnated into a square piece of filter paper each side measuring 5 cm. The treated filter paper was placed at the bottom of a 900 ml. glass bottle, and a metallic cage having a diameter of 3 cm containing ten 40-day old larvae of case-making clothes moth (*Tinea pellionella* Linne) and about 100 mg of square pieces of woollen fabrics each side measuring 3 cm was fixed at a position 5 cm above the filter paper. The bottle was then sealed up, and left to stand in a constant-temperature chamber at 25° C. for 7 hours. Then, the cage was taken out, and the mortality of the case-making clothes moth larvae was examined. Since the testing time was short, the amount of eating damage could not be evaluated. The results are shown in Table 5.

COMPARATIVE EXAMPLE 4

Example 3 was repeated except that 0.1 g of the assistant alone was used. The results are shown in Table 6.

COMPARATIVE EXAMPLE 5

Example 3 was repeated except that 0.1 g of trioxane alone was used without adding an assistant. The results are shown in Table 7.

CONTROL EXAMPLE 3

Example 3 was repeated except that no insect-proofing agent was used. The results are shown in Table 7.

TABLE 5

| Run No. | Assistant | trioxane (wt %) | assistant (wt %) | Kill ratio (%) |
| --- | --- | --- | --- | --- |
| 56 | methyl carbamate | 34 | 66 | 100 |
| 57 | dimethyl itaconate | 10 | 90 | 100 |
| 58 | p-dimethoxybenzene | 20 | 80 | 100 |
| 59 | 2,5-dimethylphenol | 70 | 30 | 100 |
| 60 | 3,4-dimethylphenol | 60 | 40 | 100 |
| 61 | 3,5-dimethylphenol | 40 | 60 | 100 |
| 62 | p-methoxyphenol | 24 | 76 | 100 |
| 63 | thymol | 20 | 80 | 100 |
| 64 | indole | 50 | 50 | 100 |
| 65 | imidazol | 70 | 30 | 100 |
| 66 | sulfolene | 25 | 75 | 100 |
| 67 | p-methyl-benzil alcohol | 30 | 70 | 100 |

TABLE 6

| Run No. | Assistant | Kill ratio (%) |
| --- | --- | --- |
| 156 | methyl carbamate | 20 |
| 157 | dimethyl itaconate | 0 |
| 158 | p-dimethoxybenzene | 10 |
| 159 | 2,5-dimethylphenol | 10 |
| 160 | 3,4-dimethylphenol | 0 |
| 161 | 3,5-dimethylphenol | 0 |
| 162 | p-methyoxyphenol | 0 |
| 163 | thymol | 0 |
| 164 | indole | 10 |
| 165 | imidazol | 0 |
| 166 | sulfolene | 10 |
| 167 | p-methyl-benzil alcohol | 30 |

TABLE 7

| Ex. No. | Insect-proofing agent | Kill ratio (%) |
| --- | --- | --- |
| Comparative Example 5 | trioxane alone | 60 |
| Control Example 3 | None | 0 |

The results of the foregoing Examples and Comparative Examples demonstrate that the trioxane compositions of this invention show better insect-proofing activity than trioxane or the assistants each used singly.

EXAMPLE 4

In each run, predetermined amounts of trioxane and an assistant were mixed, and melted in a hot water bath to form a uniform trioxane composition. The flash point of this composition was measured in accordance with ASTM by a Setaflash ® Closed-Cup Apparatus. The results are shown in Table 8.

COMPARATIVE EXAMPLE 6

The flash point of trioxane alone was measured as in Example 4. The result is also shown in Table 8.

TABLE 8

| Run No. | Assistant | trioxane (wt %) | assistant (wt %) | flash point (°C.) |
| --- | --- | --- | --- | --- |
| 68 | methyl cinnamate | 37 | 63 | 45 |
| 69 | methyl carbamate | 34 | 66 | 45 |
| 70 | dimethyl phthalate | 15 | 85 | 45 |
| 71 | dicyclohexyl phthalate | 10 | 90 | 51 |
| 72 | dimethyl isophthalate | 32 | 68 | 47 |
| 73 | dimethyl oxalate | 50 | 50 | 44 |
| 74 | benzophenone | 17 | 83 | 45 |
| 75 | p-methoxyphenol | 24 | 76 | 45 |
| 76 | thymol | 20 | 80 | 45 |
| 77 | sulfolene | 25 | 75 | 45 |
| 78 | p-methyl-benzyl alcohol | 30 | 70 | 51 |
| Comparative Example 6 | trioxane alone | 100 | 0 | 40 |

EXAMPLE 5

Trioxane and p-methylbenzyl alcohol were mixed in a weight ratio of 3:7, melted unformly at 70° C., and then cooled to 20° C. to form a solid composition. The solid composition could easily be pulverized to a uniform powder in a mortar.

The resulting composition in powder form (0.5 g) was placed at the bottom of a 500 ml glass bottle, and a metallic cage having a diameter of 3 cm containing ten 35-day old larvae of case-making clothes moth (*Tinea pellionella* Linne) and about 100 mg of square pieces of woollen fabrics each side measuring 2 cm was fixed at a position 5 cm above the powdery composition. The bottle was then sealed up, and left to stand in a constant-temperature chamber at 30° C. for 5 days. Then, the cage was taken out, and the mortality of the case-making clothes moth larvae, and the amount of eating damage of the woollen fabrics (weight loss) were examined. The results are shown in Table 9.

COMPARATIVE EXAMPLE 7-8

Example 5 was repeated except that p-methylbenzyl alcohol and trioxane in powder form was used respectively alone in the insect-proofing test. The results are shown in Table 9.

COMPARATIVE EXAMPLE 9

Example 5 was repeated except that no insect-proofing agent was used. The results are shown in Table 9.

TABLE 9

| Ex. No | Insect-proofing agent | Number of dead insects | Amount of eating damage (mg) |
|---|---|---|---|
| Example 5 | p-methylbenzyl alcohol/ trioxane composition (7:3 by weight) | 10 | 0 |
| Comparative Example 7 | p-methylbenzyl alcohol (alone) | 8 | 12 |
| Comparative Example 8 | trioxane (alone) | 10 | 0 |
| Comparative Example 9 | none | 0 | 35 |

We claim:
1. A trioxane composition having increasing insect proofing action of trioxane comprising as active ingredients
   (A) 10 to 50% by weight, of the total composition, of 1,3,5-trioxane, and
   (B) 50 to 90% by weight, of the total composition, of methyl carbamate as an assistant.

* * * * *